(12) United States Patent
Hiramatsu et al.

(10) Patent No.: US 7,401,971 B2
(45) Date of Patent: Jul. 22, 2008

(54) METHOD FOR STIRRING LIQUID

(75) Inventors: Hisao Hiramatsu, Kyoto (JP); Hironobu Ohta, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 09/817,251

(22) Filed: Mar. 27, 2001

(65) Prior Publication Data

US 2001/0028601 A1    Oct. 11, 2001

(30) Foreign Application Priority Data

Mar. 27, 2000   (JP)  ............ P. 2000-085602

(51) Int. Cl.
    *B01F 5/02*      (2006.01)
    *G01N 33/49*      (2006.01)

(52) U.S. Cl. ............ 366/131; 366/137; 366/348; 422/100

(58) Field of Classification Search ............ 366/167.1, 366/191, 136, 137, 261, 267, 269, 348, 349, 366/279, 173.1, 129, 163.1, 164.2, 164.1, 366/275; 99/345, 346, 347; D7/669; 446/176, 446/180, 197; 472/128; 222/79; 422/100
See application file for complete search history.

(56) References Cited

U.S. PATENT DOCUMENTS

| | | | | |
|---|---|---|---|---|
| 25,038 A | * | 8/1859 | Parker | 366/269 |
| 160,815 A | * | 3/1875 | Cline | 366/269 |
| 694,210 A | * | 2/1902 | Soellner | 366/269 |
| 1,031,526 A | * | 7/1912 | Cloud, Jr. | 124/65 |
| 1,400,309 A | * | 12/1921 | Munsing | 366/129 |
| 1,588,693 A | * | 6/1926 | Blum | 366/269 |
| 2,234,884 A | * | 3/1941 | Teel | 99/346 |
| 2,330,149 A | * | 9/1943 | Schaaff | |
| 2,432,073 A | * | 12/1947 | Hargen | 99/345 |
| 2,967,768 A | * | 1/1961 | Harders | |
| 3,166,300 A | * | 1/1965 | Richter | |
| 3,290,946 A | * | 12/1966 | Pursell | 73/864.15 |
| 3,295,523 A | * | 1/1967 | Weichselbaum | D7/669 |
| 3,320,053 A | | 5/1967 | Lehman | |
| 3,447,787 A | * | 6/1969 | Van Der Lely | |
| 3,468,525 A | * | 9/1969 | Kawawa | |
| 3,656,351 A | * | 4/1972 | Raczak | |
| 3,712,591 A | * | 1/1973 | Booth et al. | 366/275 |
| 4,077,629 A | * | 3/1978 | Chestney | 273/349 |
| 4,332,484 A | * | 6/1982 | Peters | |
| 4,436,822 A | | 3/1984 | Eseifan | |

(Continued)

FOREIGN PATENT DOCUMENTS

EP      0 527 059 A1    2/1993

(Continued)

OTHER PUBLICATIONS

Translation of JP 62-184357, Schrieber Translastions, Inc, Feb. 2005, 13 pages.*

*Primary Examiner*—Tony G Soohoo
(74) *Attorney, Agent, or Firm*—Sughrue Mion, PLLC

(57) ABSTRACT

A method for stirring a liquid, comprising: sucking a part of a liquid from a liquid-containing container which opens at the top thereof; and discharging the sucked liquid into the container at a discharging position which is horizontally different from a sucking position where the liquid has been sucked, and an apparatus used for the method.

14 Claims, 1 Drawing Sheet

U.S. PATENT DOCUMENTS

| | | | |
|---|---|---|---|
| 4,449,827 A * | 5/1984 | Karkiewicz | 366/275 |
| 4,452,634 A * | 6/1984 | Oguchi et al. | |
| 4,512,665 A * | 4/1985 | Cline et al. | |
| 4,612,044 A * | 9/1986 | Kutscher et al. | |
| 4,861,554 A | 8/1989 | Sakuma | |
| 5,052,813 A * | 10/1991 | Latto | |
| 5,174,162 A * | 12/1992 | Miyake et al. | 73/864.21 |
| 5,297,980 A * | 3/1994 | Barthold | 446/180 |
| 5,300,232 A * | 4/1994 | Barrington et al. | |
| 5,365,798 A * | 11/1994 | Kressirer | 73/864.11 |
| 5,383,372 A * | 1/1995 | Qureshi et al. | 73/864.17 |
| 5,452,619 A * | 9/1995 | Kawanabe et al. | 73/864.01 |
| 5,482,863 A | 1/1996 | Knobel | |
| 5,482,864 A | 1/1996 | Knobel | |
| 5,555,767 A * | 9/1996 | Makino et al. | 73/863 |
| 5,810,473 A * | 9/1998 | Manabe et al. | |
| 5,820,824 A * | 10/1998 | Tanaka | 422/100 |
| 6,254,832 B1 * | 7/2001 | Rainin et al. | 422/100 |

FOREIGN PATENT DOCUMENTS

| | | | |
|---|---|---|---|
| EP | 0 607 442 A1 | | 4/1993 |
| EP | 0 670 483 A2 | | 9/1995 |
| EP | 1 1138 372 | * | 4/2001 |
| JP | 62-184357 | | 8/1987 |
| JP | 64-27626 | | 1/1989 |
| JP | 01212356 | * | 8/1989 |
| JP | 03170046 | * | 7/1991 |
| JP | 6-39266 | | 2/1994 |
| JP | 7-55818 | | 3/1995 |
| JP | 08297125 | * | 11/1996 |
| JP | 09171024 | * | 6/1997 |
| JP | 2001-343310 | * | 12/2001 |
| WO | WO 93/25309 | | 12/1993 |

* cited by examiner

METHOD FOR STIRRING LIQUID

BACKGROUND OF THE INVENTION

1. Field of the Invention

The present invention relates to a method for stirring a liquid such as blood or the like, and an apparatus used for the method.

2. Discussion of the Background Art

In order to inspect a liquid specimen such as blood or the like, a specimen in a specimen container is normally dispensed into each container using a dispensation device having a nozzle every inspection to be conducted. However, in order to conduct accurate inspection, the concentration of components in each specimen thus dispensed must be the same. Accordingly, it is necessary to stir the specimen in the specimen container prior to dispensation so that the concentration of components is uniform all over the specimen.

As a method for stirring a liquid specimen such as blood or the like, a method using a stirring bar is known. However, if a device for stirring the specimen is provided or if a function of stirring the specimen is added to the dispensation device, the cost increases. Furthermore, in order to prevent contamination, it is necessary to add a function of washing the stirring bar to the dispensation device so that the dispensation device becomes large.

Therefore, a method using a nozzle of the dispensation device is often applied to stir a specimen. According to this method, a part of a specimen in a specimen container is sucked through the nozzle, and then kept in a tip capped on the forward end of the nozzle. Subsequently, the sucked specimen is discharged into the specimen container from the tip. As a result, the specimen is stirred.

However, this method has a poor efficiency. Therefore, in order to stir the specimen thoroughly, the suction and discharge of the specimen must be repeated many times. When the specimen is blood, the nozzle must be put deep into the specimen during suction because the components are precipitated at the bottom. Therefore, the amount of the specimen attached to the surface of the tip increases so that much time is required to clean the tip after stirring.

SUMMARY OF THE INVENTION

An object of the present invention is to provide a method for stirring a liquid thoroughly and easily.

This and other objects of the present invention have been accomplished by a method for stirring a liquid, comprising:

sucking a part of a liquid from a liquid-containing container which opens at the top thereof; and discharging the sucked liquid into the container at a discharging position which is horizontally different from a sucking position where the liquid has been sucked.

Furthermore, this and other objects of the present invention have been accomplished by an apparatus for stirring a liquid in a container, comprising:

a container in which a liquid is contained; and a means for sucking the liquid from the container and for discharging the liquid into the container, wherein the container opens at the top thereof, and wherein the means is capable of horizontally moving so that the liquid is discharged into the container at a position different from that where the liquid has been sucked from the container.

DETAILED DESCRIPTION OF THE INVENTION

Figure 1A:
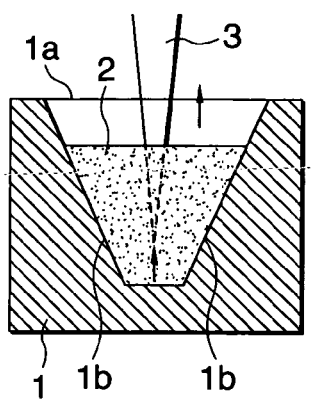
FIGS. 1(A), (B), (C), (D), (E) and (F) are diagrams illustrating an embodiment of the method for stirring a liquid according to the present invention.

According to the method of the present invention, the discharging position moves horizontally from the sucking position. When the liquid is discharged, the liquid flows downward at the discharging position while it flows upward at the sucking position in the liquid tank. As a result, convection occurs in the liquid so that the liquid is stirred by the convection. In other words, according to the method of the present invention, the liquid is efficiently stirred by the convection so that sufficient stirring can easily be carried out. Furthermore, according to the method of the present invention, it is economically advantageous because the liquid can be stirred by only providing a liquid-sucking and -discharging means such as nozzle or the like. Moreover, according to the method of the present invention, even if the specimen is a liquid of which components are liable to precipitate, such as blood or the like, the precipitated components can be diffused into the entire liquid with the convection currents so that it is not necessary to suck the liquid from the depth of the liquid. Accordingly, the tip used can easily be subjected to cleaning or other post-treatments.

In order to stir the liquid thoroughly, the suction and discharge of the liquid are preferably repeated plural times. In this case, it is preferred that the discharging position of n times (n represents an integer of 2 or more) moves horizontally from the discharging position of n−1 time(s). Accordingly, the direction of the discharging position toward the sucking position changes from the n−1 times(s) to the n times so that the direction of convection changes from the n−1 time(s) to the n times. Therefore, the liquid can be stirred more efficiently. A moving method of the discharging position is not particularly limited. For example, however, the discharging positions can be changed between the left end and the right end of the container by turns. Also, the sucking positions can be changed from the n−1 time(s) to the n times, instead of the change of the discharging position, or the discharging position of n times can be changed from the sucking position of n−1 time(s). The same effects can be obtained by these changes. These changes can be carried out by hand or automatic control.

Moreover, when the liquid is discharged into the container, the air can be supplied to the means for sucking and discharging the liquid. The air is discharged together with the liquid.

The shape of the container used in the present invention is not particularly limited. For example, it may be cylindrical, conical, cubic, or the like, and may have a round bottom, a flat bottom, or the like. However, the container for containing the liquid preferably has an inclination on the inside wall thereof which increases in height toward the outside of the container so that the liquid can be discharged toward the inclination. In this manner, the discharge of the liquid causes the liquid to flow along the inclination in the vicinity of the side wall of the container. Since the inclination increases in height toward the outside of the container, the liquid flow thus generated is oblique downward, that is, the liquid flows downward toward the sucking position. In this manner, a vigorous convection can be generated so that the liquid can be stirred more efficiently. The inclination in the container of this arrangement can be provided at a proper height on the inside wall thereof. Additionally, the entire part ranging from the bottom to the opening can form an inclination. The inclination may be straight or curved, so long as it increases in height toward the outside of the container.

Furthermore, the liquid may be sucked from or discharged into the container vertically or obliquely by tilting the container, the nozzle or the like.

In the present invention, any container can be used, so long as the material of the container does not have an influence on a specimen such as blood or the like. Examples of the material include glass, plastic, resin and the like.

Also, the size of the apparatus of the present invention, including the container and the means for sucking and discharging a liquid, is not particularly limited.

According to the method of the present invention, a liquid can be stirred efficiently, and treatment after stirring can be easily effected. Furthermore, according to the method of the present invention, a dispensation device for stirring the liquid can be provided economically.

EXAMPLE

Figure 1B:
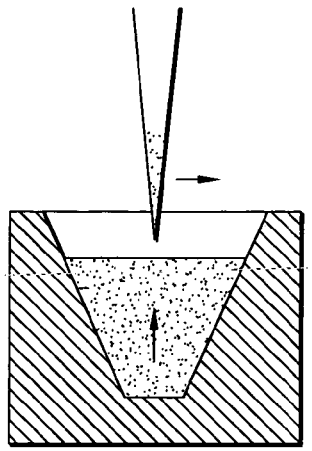
Figure 1C:
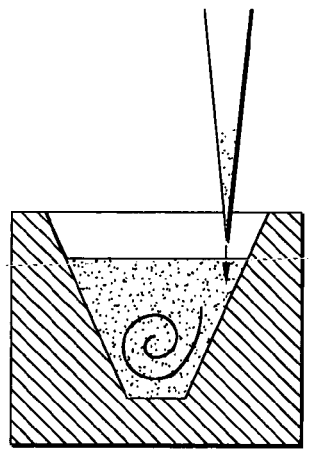
Figure 1D:
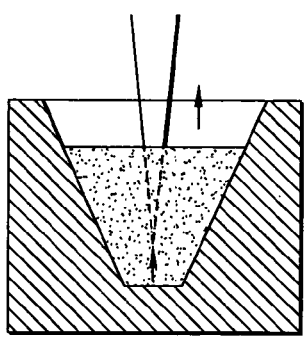
Figure 1E:
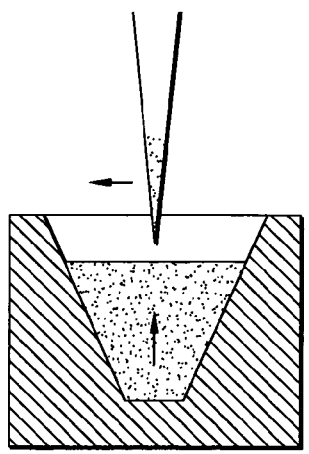
Figure 1F:
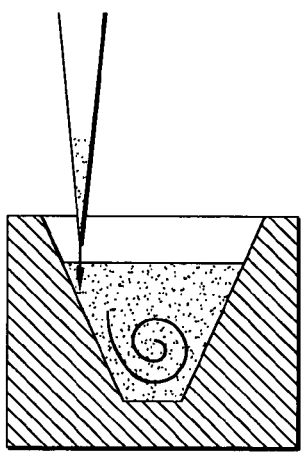

An embodiment of implication of the present invention will be explained based on FIG. 1.

A container 1 for a specimen used in the present embodiment is cylindrical and has an opening 1a at the top thereof. The inside wall of the specimen container 1 forms an inclination surface 1b which increases in height toward the outside of the container 1. Thus, the inside of the container 1 is in the form of inverted cone. The container 1 contains a liquid specimen 2. According to the method of the present embodiment, the specimen 2 is stirred as follows.

At first, a nozzle 3 having a tip capped on the forward end thereof is prepared. As shown in FIG. 1 (A), the nozzle 3 is put down into the central part of the container 1 through the opening 1a to suck a part of the specimen 2. Subsequently, as shown in FIG. 1 (B), the nozzle 3 is moved upward to a position above the liquid level, and then is moved to right. At this time, the specimen 2 flows upward in the central part of the container 1 from which the specimen has been sucked. After the nozzle 3 is moved close to the right end of the container 1, the sucked specimen is then discharged toward the inclination 1b, as shown in FIG. 1 (C), optionally together with the air. The specimen 2 in the vicinity of the right end of the container 1 flows downward toward the central part of the container along the inclination 1b. Since the specimen 2 flows upward in the vicinity of the central part of the specimen tank 1, a convection occurs inside the specimen. As a result, the specimen 2 can be stirred by the convection.

Next, the nozzle 3 is moved to the central part of the container 1 where a part of the specimen 2 is then again sucked, as shown in FIG. 1 (D). As shown in FIG. 1 (E), the nozzle 3 is moved upward, and then is moved to left. The sucked specimen is then discharged in the vicinity of the left end of the container 1, as shown in FIG. 1 (F), optionally together with the air. In this manner, a convection occurs in the direction opposite to that of the convection generated as shown in FIG. 1 (C) to stir the specimen again. When the steps (A) to (F) are repeated several times, the concentration of components is uniform all over the entire part of the specimen. In order to stir another specimen, only the tip of the nozzle 3 can be replaced prior to stirring in the same manner.

According to the method of the present embodiment, a dispensation device having a nozzle 3 can be used to stir the specimen 2. Therefore, no special stirring device or function is required so that the cost becomes lower. Since convection is used in the method of the present embodiment, the direction of the convection differs between the step of FIG. 1 (C) and the step of FIG. 1 (F), the specimen 2 can be stirred thoroughly and easily. Furthermore, according to the present embodiment, even the components which have been precipitated on the bottom of the container 1 can be moved up with the convection so that it is not necessary that the nozzle 3 is put down into the depth of the specimen 2 in suction. Accordingly, even when the specimen 2 is blood, the amount of the specimen attached to the tip of the nozzle 3 can be reduced so that the tip can easily be cleaned.

In the present embodiment, the discharging position of the specimen 2 is moved horizontally to cause convection currents in different directions, but the present invention is not limited thereto. For example, the sucking position can be moved, instead of the discharging position. Alternatively, both the discharging position and the sucking position can be moved. In order to minimize the amount of the specimen attached to the tip, the angle of the inclination 1b to the bottom of the specimen tank may be increased to lower the liquid level.

This application is based on Japanese application No. 2000-085602, the entire content of which is incorporated herein by reference.

While the invention has been described in detail and with reference to specific embodiments thereof, it will be apparent to one skill in the art that various changes and modifications can be made therein without departing from the spirit and scope thereof.

What is claimed is:

1. A method for stirring a liquid, comprising:
   sucking a part of a liquid into a nozzle from a liquid-containing container which opens at the top thereof; and
   discharging the sucked liquid from the same nozzle directly into liquid remaining in the container at a discharging position above the surface of the liquid remaining in the container and which is horizontally different from a sucking position where the liquid has been sucked to thereby stir the liquid,
   wherein the sucking and the discharging positions are controlled by automatic control,
   wherein said sucking and said discharging are conducted plural times,
   wherein the container has an inclination on the inside wall thereof, said inclination increasing in height toward the outside of the container, and the sucked liquid is discharged toward the inclination,
   wherein the discharged position is limited to a position which is horizontally external to the sucked position,
   wherein the liquid is blood.

2. The method according to claim 1, wherein the sucked liquid is discharged together with air, wherein the nozzle contains air before and during the sucking step.

3. The method according to claim 1, wherein the discharging position of n times is horizontally different from the discharging position of n-1 time(s), and wherein n represents an integer of 2 or more.

4. The method according to claim 1, wherein the sucking position of n times is horizontally different from the sucking position of n-1 time(s), wherein n represents an integer of 2 or more.

5. The method according to claim 1, which is used in an inspection apparatus.

6. The method according to claim 1, wherein the sucked position is near the center of the container.

7. The method according to claim 1, wherein the liquid is sucked at the deepest position of the container and subsequently discharged toward an inclination of the container to stir the liquid by convection.

8. A method for stirring a liquid, comprising:

sucking a part of a liquid into a nozzle from a liquid-containing container which opens at the top thereof and has an inclination on the inside wall thereof; and discharging the sucked liquid from the same nozzle directly toward the inclination at a discharging position above the surface of the liquid remaining in the container and which is horizontally different from a sucking position where the liquid has been sucked to thereby stir the liquid, wherein the sucking and the discharging positions are controlled by automatic control wherein said sucking and said discharging are conducted plural times, wherein the inclination increases in height toward the outside of the container, wherein the discharged position is limited to a position which is horizontally external to the sucked positions, wherein the liquid is blood.

9. The method according to claim 8, wherein the sucked liquid is discharged together with air, wherein the nozzle contains air before and during the sucking step.

10. The method according to claim 8, wherein the discharging position of n times is horizontally different from the discharging position of n-1 time(s), and wherein n represents an integer of 2 or more.

11. The method according to claim 8, wherein the sucking position of n times is horizontally different from the sucking position of n-1 time(s), and wherein n represents an integer of 2 or more.

12. The method according to claim 8, which is used in an inspection apparatus.

13. The method according to claim 8, wherein the sucked position is near the center of the container.

14. The method according to claim 8, wherein the liquid is sucked at the deepest position of the container and subsequently discharged toward the inclination of the container to stir the liquid by convection.

\* \* \* \* \*